United States Patent [19]
Jacques et al.

[11] Patent Number: 5,981,838
[45] Date of Patent: Nov. 9, 1999

[54] GENETIC MANIPULATION OF PLANTS TO INCREASE STORED CARBOHYDRATES

[76] Inventors: Nicholas Anthony Jacques, 24 Moncrieff Dr., East Ryde, Australia, 2113; Christine Lynn Simpson, Flat 0, Ashtree House Claremont Road, Newcastle-upon-Tyne, United Kingdom, NE2 4AN; Philip Morrison Giffard, 12 Myuna Street, Balmoral, Australia, 4171

[21] Appl. No.: 08/793,824
[22] PCT Filed: Aug. 24, 1995
[86] PCT No.: PCT/AU95/00527
  § 371 Date: Apr. 25, 1997
  § 102(e) Date: Apr. 25, 1997
[87] PCT Pub. No.: WO96/06173
  PCT Pub. Date: Feb. 29, 1996

[30] Foreign Application Priority Data

Aug. 24, 1994 [AU] Australia ................ PM 7643

[51] Int. Cl.⁶ .......... C12N 15/82; C12N 15/54; C12N 15/31; C12P 19/04; C12P 19/18
[52] U.S. Cl. .......... 800/284; 800/288; 800/298; 435/69.1; 435/101; 435/193; 435/320.1; 435/468; 536/23.7
[58] Field of Search ........... 800/205, 284, 800/288, 298; 536/23.7; 435/69.1, 101, 172.3, 193, 320.1, 468

[56] References Cited

FOREIGN PATENT DOCUMENTS

| | | |
|---|---|---|
| 46881/89 | 6/1990 | Australia . |
| WO 89/12386 | 12/1989 | WIPO . |
| WO 90/02484 | 3/1990 | WIPO . |
| WO 92/11382 | 7/1992 | WIPO . |
| WO 94/11520 | 5/1994 | WIPO . |

OTHER PUBLICATIONS

*Streptococcus salivarius* ATCC 25975 Possesses at Least Two Genes Coding for Primer–Independent Glucosyltransferases, Christine L. Simpson, et al., Infection and Immunity, Feb. 1995, pp. 609–621, Vo. . 63, No. 2.

Sequence of the gtfK gene of *Streptococcus salivarius* ATCC 25975 and evolution of the gtf genes of orgal streptococci, Philip M. Giffard, et al., Journal of General Microbiology (1993), 139, pp. 1511–1522.

Chemical Composition and in vitro Digestibility of Lines of *Lolium perenne* Selected for High Concentrations of Water–soluble Carbohydrate, I. Radojevic, et al., Aust. J. Agric. Res., (1994), 45, pp. 901–912.

Glucosyltransferases of Oral Streptococci, Nick Jacques, et al., Today's Life Science, Mar. 1991, 40–46.

Reprints from Reizer & Peterkofsky: Sugar Transport and Metabolism in Gram–Positive Bacteria, Published in 1987 by Ellis Horwood Ltd., Chichester, England, ISBN 0–7458–0024–6, Walker et al, pp. 39–68, Chapter 2.

Analysis of the *Streptococcus downei* gtfS Gene, Which Specifies a Glucosyltransferase That Synthesizes Soluble Glucans, N. A. Jacques, Keeta S. Gilmore, et al., Infection and Immunity, Aug. 1990, pp. 2452–2458, vol. 58, No. 8.

(List continued on next page.)

*Primary Examiner*—David T. Fox
*Attorney, Agent, or Firm*—Kirschstein, et. al.

[57] ABSTRACT

The present invention relates to plants genetically modified to increase the level of stored carbohydrates in the plant, particularly during periods of high sink activity and low source activity through production of a glycosyl-transferase which catalyzes the formation of soluble glucans. The invention also relates to the genetic constructs used to produce the engineered plants and the method of producing the engineered plants.

17 Claims, 1 Drawing Sheet

OTHER PUBLICATIONS

Molecular characterization of a cluster of at least two glucosyltransferase genes in *Streptococcus salivarius* ATCC 25975, Philip M. Giffard, et al., Journal of General Microbiology (1991), 137, pp. 2577–2593.

Cloning and Expression of Glycosyltransferase Activities from *Streptococcus salivarius*, L.J. Pitty, et al., Journal of Dental Research, Special Issue, 1989, vol. 68 : 1681–1682, Nov.

Membrane Perturbation by Cerulenin Modulates Glucosyltransferase Secretion and Acetate Uptake by *Streptococcus salivarius*, Nicholas A. Jacques, Institute of Dental Research, Journal of Microbiology (1983), 129, pp.3293–3302.

The glucosyltransferases of *Streptococcus salivarius*, Nicholas A. Jacques, Australian Dental Journal 1994; 39(2):111–114.

Sequence Analysis of the gtfB Gene from *Streptococcus mutans*, T. Shiroza, et al., Journal of Bacteriology, Sep. 1987, pp. 4262–4270, vol. 169, No. 9.

Extracellular Sucrose Metabolism by *Streptococcus salivarius*, N. A. Jacques, Institute of Dental Research, 1995, vol. 85, pp. 315–322, Dev. Biol. Stand.

Nucleotide Sequence of a Glucosyltransferase Gene from *Streptococcus sobrinus* MFe28, Joseph J. Ferretti, et al., Journal of Bacteriology, Sep. 1987, pp. 4271–4278, vol. 169, No. 9.

Fructan as a New Carbohydrate Sink in Transgenic Potato Plants, Ingrid M. van der Meer, at al., Gene Plant Cell, vol. 6, pp.561–570, Apr. 1994, American Society of Plant Physiologists.

Accumulation of Fructose Polymers in Transgenic Tobacco, Michael J. M. Ebskamp, et al., Biotechnology, vol. 12, pp. 272–275, Mar. 1994.

Table 1 — Properties of the GTFs of *Streptococcus salivarius* ATCC 25975 May 1994.

Definition of a Fundamental Repeating Unit in Streptococcal Glucosyltransferase Glucan–binding Regions and Related Sequences, P. M. Giffard, et al., Journal of Dental Research, vol. 73, No. 6, pp. 1133–1141, 1994.

Kossmann et al. Progress Biotechnol. 10:271–278, 1995.

Simpson et al., *Microbiology*, vol. 141, pp. 1451–1460 (1995).

GENETIC MANIPULATION OF PLANTS TO INCREASE STORED CARBOHYDRATES

This application is a 371 of PCT/AU95/00527 filed Aug. 24, 1995.

TECHNICAL FIELD

The present invention relates to plants genetically modified to increase the level of stored carbohydrates in the plant, particularly during periods of high sink activity and low source activity. The invention also relates to the genetic constructs used to produce the engineered plants and the method of producing the engineered plants.

BACKGROUND ART

The soluble storage carbohydrate found in plants, including sucrose, glucans, starch and fructans, are an important source of feed for animals, particularly grazing ruminants. These carbohydrates are stored non-structurally which makes them readily available for digestion by animals and therefore an important source of digestible energy.

During periods of high sink activity and low source activity, such as during a drought, the level of stored carbohydrates falls as the non-structural storage carbohydrates are mobilised for use in seed filling. The result of this mobilisation, particularly in relation to pasture grasses, is a significant loss of feed value to grazing ruminants due to the reduction in the levels of the stored carbohydrates. This reduction is caused by the enzymatic degradation of the stored carbohydrates. This enzymatic degradation is assisted by the fact that the stored carbohydrates generally have a low degree of polymerization. For example, as noted by Radojevic et al 1994, during the period from late spring to early autumn in southern Australia, the declining feed quality of the grasses causes a corresponding reduction in the lactation by dairy herds and necessitates the use of supplementary feeds. This decline in digestibility is associated with a decline in the level of soluble carbohydrates.

Perennial rye grass lines which accumulate high concentrations of soluble carbohydrates from late spring to early autumn do not suffer as large a decline in digestibility (Radojevic et al 1994). The result of this increased digestibility is a corresponding increase in milk production by dairy herds.

In addition to this, there are many pasture plants, such as white clever which do not possess any significant levels of stored carbohydrate.

There has, therefore, been a desire to develop methods for preventing the degradation of the stored carbohydrates during plant senescence and to increase the level of stored carbohydrates in pasture plants with low levels.

Glucosyltransferases of *Streptococcus salivarius*

It is known that many strains of *Streptococcus salivarius* and *Streptococcus mutans*, produce extracellular α-D-glucosyltransferase (Gtfs), an enzyme which catalyses the formation of glucan from sucrose. These Gtfs are also found in many other species of oral streptococci.

The Gtfs utilise the high free energy of the glycosidic bond of sucrose to synthesise glucans (Jacques N A, Giffard P M, 1991). Gtfs produce either soluble or insoluble products by transferring a glucose residue from sucrose to a growing glucan chain.

Gtfs which produce an insoluble product are generally considered to be primer-dependent (Walker G J, Jacques N A, 1987). These primer-dependent Gtfs require a dextran (α-(1→6)-linked glucan) as a receptor for polymerisation to proceed at an appreciable rate. In contrast, Gtfs that produce soluble products may be either primer-dependent or primer-independent. The genetic sequences for 10 gtf genes from a number of Streptococcus species have been ascertained (Gilmore K S, Russell R R B, Ferretti J J). All the Gtfs coded by these genes possess highly conserved putative signal sequences that lead to the secretion of these enzymes. The remainder of each protein is arbitrarily divided into two domains—the N-terminal two-thirds "catalytic domain" and the C-terminal one-third "glucan-binding domain".

*S. salivarius* ATCC 25975 has been shown to possess at least four different gtf genes (Giffard et al (1991); Giffard et al (1993)). Each of these genes codes for a highly hydrophilic monomeric glucosyltransferase that possesses unique enzymic properties. These Gtfs synthesize structurally different glucans from sucrose. For example, the genes coding for GtfJ and GtfL produce enzymes which synthesize insoluble glucans. GtfJ is a primer-dependent enzyme producing essentially a linear a(1→3)-glucan while GtfL is a primer-independent enzyme that synthesizes a glucan containing 50% α-(1→3)—and 50% α-(1→6)-linked glucosyl residues. In contrast, the gtfK and gtfM genes code for enzymes which produce a soluble glucan which possess α-(1→6)-linked glucosyl residues. GtfK is primer stimulated while GtfM is primer independent.

SUMMARY OF THE INVENTION

Up until now, a gtf gene in *S. salivarius* or any other Streptococcus species which produces a glucosyltransferase that synthesises a glucan which is both soluble and primer independent has not been described.

The significance of a glucosyltransferase produced by *S. salivarius*, or any other streptococci, which is both primer independent and which synthesises a soluble glucan product is twofold. First, the primer independence of the Gtf means that the enzyme should be functional when expressed in plants while the glucan that is formed from sucrose in the plant should be readily stored without detriment to the plant, due to its solubility.

An important characteristic of soluble glucans produced by Gtf synthesis is that they are poorly degraded by plant enzymes and are readily digested by the diverse microflora present in the rumen of grazing livestock.

The inventors of the present invention have isolated and characterised a novel gtf (GtfM) gene in *S. salivarius* which codes for a primer independent Gtf which produces a glucan which is soluble, resistant to degradation by plant enzymes and readily digested by microflora present in the rumen of grazing livestock.

According to a first aspect of the present invention there is provided a plant containing bacterial DNA which codes for a glucosyltransferase which catalyses the formation of glucans from sucrose.

Preferably, the plant contains bacterial DNA which codes for a glucosyltransferase which is primer independent.

More preferably, the plant contains DNA which codes for a glucosyltransferase which catalyses the formation of soluble glucans.

More preferably, the bacterial DNA is obtained from *Streptococcus salivarius*.

According to a second aspect of the present invention there is provided a DNA comprising a sequence according to SEQ ID NO: 1.

According to a third aspect of the present invention there is provided a DNA sequence which is a variant of a DNA having a sequence according to SEQ ID NO: 1. In this respect a "variant" is a polynucleotide which corresponds to or comprises a portion of the DNA of the invention, or is "homologous" to the DNA of the invention. For the purposes of this description, "homology" between two polynucleotide sequences connotes a likeness short of identity, indicative of a derivation of the first sequence from the second. In particular, a polynucleotide is "homologous" to the DNA of the invention if there is greater than 70% identity in the DNA sequence.

The polynucleotides of the present invention exclude those polynucleotides in the environment in which they occur in nature. They include the polynucleotides in a form in which the are substantially free of other *Streptococcus salivarius* polynucleotide sequences, such as sequences in isolated form, including those in substantially purified form.

According to a fourth aspect of the present invention there is provided a protein comprising the amino acid sequence according to SEQ ID NO: 2.

According to a fifth aspect of the invention there is provided a polypeptide comprising an amino-acid sequence which is a variant of SEQ ID NO:2. A variant is a polypeptide which corresponds to or comprises a portion of the polypeptide of the invention, or is "homologous" to the peptide of the invention. For the purposes of this description, "homology" between two peptide sequences connotes a likeness short of identity, indicative of a derivation of the first sequence from the second. In particular, a polypeptide is "homologous" to the peptide of the invention if there is greater than 70% identity in the amino acid sequence.

These homologous polypeptides can be produced by conventional site-directed mutagenesis of the corresponding DNA or by chemical synthesis, and fall within the scope of the invention, particularly where they retain the biological activity of a glucosyltransferase.

The proteins and polypeptides of the invention exclude those proteins and polypeptides in the environment in which they occur in nature. They include the proteins and polypeptides in a form in which they are substantially free of other *Streptococcus salivarius* polypeptide sequences, such as sequences in isolated form, including those in substantially purified form.

According to a sixth aspect of the present invention there is provided the microorganism *E. coli* containing plasmid pGSG501.

According to a seventh aspect of the present invention there is provided the microorganism *E. coli* containing plasmid pGSG502.

According to a eighth aspect of the present invention there is provided a plant containing DNA comprising a sequence according to SEQ ID NO: 1.

According to an ninth aspect of the present invention there is provided a plant containing DNA which is a variant of DNA having a sequence according to SEQ ID NO: 1.

According to a tenth aspect of the present invention there is provided a plant expressing a protein comprising an amino acid sequence according to SEQ ID NO: 2 or a variant thereof.

DNA and variants thereof of the invention can be incorporated into a variety of plant types. These include plants, such as grasses, used as fodder for livestock. They also include cereal crops or other starchy food product types, (to provide grain or other food with increased fibre); and horticultural crops, such as tomatoes and fruits, to provide fruits with increased solids.

In addition plants expressing the DNA and variants thereof, of the invention may also produce dextran which can in turn be used:

1) as a binder for use in processed foods (e.g. so called 'health bars');

2) in pharmaceutical preparations again as a binder; and 3) in medical preparations to increase antigenic activity.

DETAILED DESCRIPTION OF THE INVENTION

Figure 1:
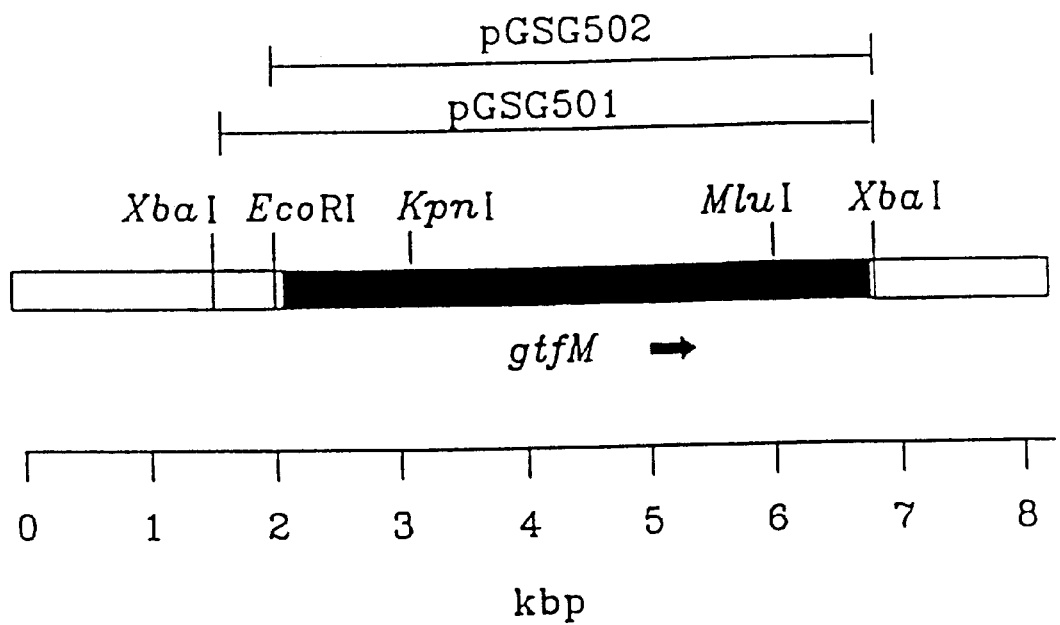
FIG. 1 shows a restriction map of the inserts from pGSG501 and pGSG502.

The invention is further described with reference to the accompanying Example which is no way limiting on the scope of the present invention.

Example 1

The general strategy adopted to isolate a gene from *S. salivarius* encoding a Gtf which produces a primer independent and soluble glucan is as follows:

A λ gene bank containing *S. salivarius* DNA was prepared. Positive clones were detected by using an *E. coli* strain grown on agar containing sucrose. *E. coli* which contained gtf DNA from *S. salivarius* could convert the sucrose in the medium into a polymer which resulted in opaque colonies. These opaque colonies were then picked and the *S. salivarius* DNA excised and subjected to restriction mapping to ascertain whether the DNA was from a previously described *S. salivarius* gtf gene, or whether the DNA was novel. Three clones containing novel DNA were located. These were subjected to a radioactive assay to determine whether the DNA encoded for a primer independent or primer dependent Gtf. One clone-λC-13 was found to contain a novel gtf gene which coded for a primer independent Gtf. The DNA from this clone was then isolated and sequenced.

The particular details of this methodology are now described below.

Bacterial strains and growth conditions.

*Escherichia coli* LE392 and NM522 and *S. salivarius* ATCC 25975 were used. *E. coli* strains were grown in Luria-Bertani (LB) medium at 37° C., supplemented with ampicillin (100 μg ml$^{-1}$), isopropylthiogalactoside (IPTG) (1 mM), or 5-bromo-4-chloro-3-indolyl-β-D-galactoside (X-gal) (100 μg ml$^{-1}$) as appropriate. Cultures of *S. salivarius* were grown at 37° C. in semi-defined medium (SDM) containing 25 mM glucose supplemented with 0.005μl Tween 80 ml$^{-1}$ where appropriate.

Bacteriophage and phagemids. All genetic constructs, excluding sequencing subclones, are listed in Table 1. Bacteriophage-λ derivatives were grown either as 20 ml or 1 L-liquid lysates using *E. coli* strain LE392 as the host and DNA purified according to the method of Silhavy et al (1984). Plasmids were propagated in *E. coli* strains as described previously (Giffard et al, 1991).

Screening of Gene Bank. A bacteriophage-λ gene bank of *S. salivarius* ATCC 25975 (Pitty et al, 1989) was screened by detecting plaques on a lawn of *E. coli* LE392 grown at 37° C. on minimal agar medium containing 0.2% glucose and 50 μg ml$_{-1}$ methionine as well as it (wt/vol) sucrose with or without 0.02% (wt/vol) dextran T-10. Potential Gtf clones were detected by their opacity including λC-13 containing the gtf M gene.

Twenty recombinant plaques were picked from minimal media plates containing sucrose and the EcoR1 restriction patterns of these recombinants were analysed. Of these recombinants, only λC-13 exhibited a unique EcoR1 restriction pattern and Gtf activity. A restriction map of λC-13 was constructed using double restriction digests. The Gtf gene encoded by λC-13 (GtfM) was located on an 8.3 kbp insert (see FIG. 1). The 5.3 kbp XbaI fragment from λC-13 was subcloned into pIBI31 30 (pGSG501; see Table 1) and was positive for Gtf activity as was the 4.8 kbp XbaI/EcoR1 from λC-13 subcloned into pIBI31 (pGSG502; see Table 1).

glucanase was added to a final concentration of 500 mU/ml and the solution incubated at 37° C. Duplicate aliquots (500μl) were removed and assayed for total remaining glucan at varying time intervals over a 5 h period. Any reduction in glucan (cpm) during this period was attributed to hydrolysis by the endo-(1→6)-α-D-glucanase.

DNA sequence analysis. DNA sequence determination was carried out on CsCl purified double-stranded DNA using the Pharmacia T7 sequencing kit according to the manufacturer's instructions. Custom-made oligonucleotide primers (17 mers) were used and all sequencing was con-

TABLE 1

Bacterial Strains, Phages and Phagemids

| Bacteria, Phage or Phagemid | Description | Source or reference |
|---|---|---|
| Bacterium: | | |
| *Streptococcus salivarius* ATCC 25975 | | ATCC (Hamilton, 1967) |
| *Escherichia coli* LE392 | F⁻ e14⁻(merA⁻) hsdR514 ($r_K^- m_K^-$) supE44 and supF58 lacY1 or Δ(lacIZY)6 galK2 gal722 metB1 trpR55 | Murray et al., 1977 |
| *Escherichia coli* NM522 | F'lacI$^q$ Δ(lacZ) M15 proA⁺B⁺/supE thi Δ(lac-proAB) ΔhsdMS-mcrB)5 ($r_K^- m_K^-$ McrBC⁻) | Gough and Murray, 1983 |
| Bacteriophage: | | |
| λL47.1 | | Loenen and Brammar, 1980 |
| λA-8 | λL47.1 with GtfJ encoding 8.5 kbp Sau3A partial fragment of *S. salivarius* ATCC 25975 | Pitty et al., 1989 |
| λA-33 | λL47.1 with GtfK encoding 9.6 kbp Sau3A partial fragment of *S. salivarius* ATCC 25975 | Pitty et al., 1989 |
| λC-13 | λL47.1 with 8.3 kbp GtfM encoding Sau3A partial fragment of *S. salivarius* ATCC 25975 | This study |
| λD-10 | λL47.1 with 11 kbp GtfL encoding Sau3A partial fragment of *S. salivarius* ATCC 25975 | This study |
| λD-40 | λL47.1 with Sau3A partial fragment of *S. salivarius* ATCC 25975 isolated from sucrose-containing medium | This study |
| Phagemid: | | |
| pIBI30 | Ap$^r$, f1 origin replication, β-galactosidase, T3 and T7 polymerase promoters | IBI Corporation |
| pIBI31 | Ap$^r$, f1 origin replication, β-galactosidase, T3 and T7 polymerase promoters | IBI Corporation |
| pGSG101 (pGS101) | pIBI30 with GtfJ encoding 6.8 kbp SacI/BamHI fragment of λA-8 | Giffard et al., 1991 |
| pGSG201 (pGS201) | pIBI30 with GtfK encoding 7.3 kbp BgIII/BamHI fragment of λA-33 | Giffard et al., 1991 |
| pGSG401 | pIBI30 with GtfL encoding 6.2 kbp BamHI/XbaI fragment of λD-10 | This study |
| pGSG402 | pIBI31 with 6.2 kbp BamHI/XbaI fragment of λD-10 | This study |
| pGSG403 | pIBI30 with 4.8 kbp EcoRI fragment of λD-10 | This study |
| pGSG404 | pIBI30 with 4.1 kbp EcoRI fragment of λD-10 | This study |
| pGSG502 | pIBI31 with GtfM encoding 5.3 kbp XbaI fragment of λC-13 | This study |
| pGSG502 | pIBI31 with GtfM encoding 4.8 kbp EcoRI/XbaI fragment of λC-13 | This study |
| pGSG503 | pIBI31 with 3.7 kbp KpnI/XbaI fragment of λC-13 | This study |

Detection of Gtf activity. Gtf activity was routinely detected using a qualitative microtitre reducing sugar test for liberated fructose, outlined in Jacques N. A. (1983). Gtf activity encoded by phagemids was released from *E. coli* cells by permeabalizing 1 ml of a stationary phase culture. This was achieved by vortexing the cells in the presence of 50 μl 0.1% (wt/vol) SDS and 100 μl chloroform for 20 seconds. Quantification of Gtf activity utilized [U-glucosyl-$^{14}$C]-labelled sucrose. One unit of enzyme activity was defined as the amount of Gtf that catalyzed the incorporation of 1 μmol of the glucose moiety of sucrose in 75% (vol/vol) ethanol-insoluble polysaccharide per min.

The assay mix used for the quantification of Gtf activity was scaled up to 8 ml and incubated with 3.2 ml of bacteriophage λ lysates at 37° C. for 2 h. After the 2 h incubation, the assay mix was boiled for a further 1 h to inactivate the enzyme and the amount of glucan formed (cpm) determined by assaying duplicate 500μl aliquots. After cooling to 37° C., *C. gracile* endo-(1→6)-α-D- firmed in both directions. DNA sequences were assembled and open reading frames (orfs) detected using the IBI-Pustell sequence analysis software version 2.03.

Southern Hybridizations. Chromosomal DNA from *S. salivarius* ATCC 25975 was extracted and purified as previously described (Giffard et al, 1991). Southern hybridizations were done essentially as outlined by Silhavy et al (1984) and in accordance with standard techniques such as those described in Maniatis et al (1989).

Incorporation into plants. Incorporation of gtfM gene into plants is obtained by standard transgenic techniques. The gtfM gene is obtained from λC-13 or pGSG501 by PCR. Various constructs are made using PCR primers that either do or do not contain a coding region that adds a vacuolar targeting sequence to the N- or C-terminus of the GtfM protein. These PCR constructs are cloned into a pUC18 based vector containing a Cauliflower Mosaic Virus (CaMV) 35S promoter. By this means the streptococcal promoter is replaced by a plant promoter.

Other methods of incorporating foreign DNA into plants are taught in Australian Patent Application No. 46881/89 by Ciba Geigy Ag. They include the use of *Agrobacterium tumefaciens* and the leaf disc transformation method and the use of Tobacco Mosaic Virus (TMV).

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 4853 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Streptococcus salivarius (xi) SEQUENCE DESCRIPTION: SEQ ID NO:1:

```
CAGAGATTTA TGAAAAGAAG ATGATTTTTT CCTATTTGTA ATTTGTCTGA ATATATCATA      60

GAGTAGAGAT GACAACAGAA AAAAGGATGA TTGATATAGA TGGAAAATAA GGTACGTTTT     120

AAACTACACA AGGTTAAGAA AAACTGGGTA ACTATTGGGG TGACCACTCT CTCAATGGTT     180

GCCTTGGCAG GTGGAAGCCT CCTAGCTCAA GGAAAAGTAG AGGCCGATGA GACGAGCGCA     240

CCTAACGGTG ACGGCTTGCA GCAACTGAGT GAGGATGGGA CTGCCAGTCT AGTGACGACA     300

ACAACTGTTA CTGAGCAAGC TAGTGCTCAA GCAAGTGTGT CAGCAGTAGC AACAGCCAGC     360

GTAAGTCACG AAACAAGCTT CCAGGCGGCG ACAAGTGCAG TCAGCCAGGA GGCAACTGCT     420

CAAGCACAAA CTAGTCCAGT TGCCAGTCAA GAAGTGGCAG TATCTTCGCA AACTCAATCC     480

AGTGGCCAAG AGACACAGAC TACTGAACAG GTGTCACAAG GTCAGACATC AACTCAAGTA     540

GCTGGGCAAA CAAGTGCTCA GTCTACTCCA AGTGTGACAG AACAAGCAAG ACCTAGAGTC     600

TTGACCAATG CAGCGCCAGC AATTGCCACA CGCGCTGCTG ATAGCACTAT TCGTATCAAT     660

GCCAACCGCA ATACTAACAT CACGATTACG GCCAGCGGTA CGACACCAAA TGTAACCATT     720

ATCACAGGGC CAAACACGCC TAAACCAAAC GTGACGGTGA CAAGTCCAAA TGGCACAAGA     780

CCAAATGTGA CCATTGTAAC GCAGCCAAAT CAACCCAACA AACCTGTTCA ACCAAGTCAA     840

CCGTCTCAAC CTAACAAGCC GGTCCAACCA AATCAGCCAA GTCTTGACTA TAAACCAGTA     900

GCCTCTAACT TGAAGACTAT CGATGGCAAG CAGTACTATG TTGAAAATGG CGTCGTGAAA     960

AAGAACGCAG CCATTGAGCT TGATGGGCGT CTTTATTATT TCGATGAGAC TGGAGCTATG    1020

GTGGATCAAA GTAAACCTTT GTATCGTGCC GATGCCATTC CAAATAACTC TATCTATGCG    1080

GTTTATAACC AGGCCTATGA TACGTCAAGT AAGAGTTTTG AACACTTGGA TAATTTCTTG    1140

ACGGCTGATA GCTGGTACCG TCCAAAACAG ATTTTGAAGG ATGGGAAGAA TTGGACAGCT    1200

TCAACTGAGA AAGATTATCG TCCACTTTTG ATGACTTGGT GGCCAGACAA GGTGACACAG    1260

GTCAACTACC TCAACTATAT GAGCCAACAA GGGTTTGGTA ATAAGACCTA TACGACAGAT    1320

ATGATGAGCT ATGACTTGGC AGCTGCTGCC GAAACGGTTC AACGAGGCAT CGAGGAACGT    1380

ATTGGTCGTG AGGGCAATAC CACTTGGCTT CGCCAGTTGA TGTCAGACTT CATCAAAACA    1440
```

```
CAGCCTGGCT GGAACTCTGA GAGTGAGGAC AATCTCTTAG TTGGTAAAGA CCACTTGCAA    1500

GGAGGCGCTC TGACCTTCCT AAATAATAGT GCGACAAGTC ATGCCAATTC AGATTTCCGC    1560

CTCATGAACC GCACACCGAC TAACCAAACG GGGACACGCA AATATCATAT TGACCGTTCA    1620

AATGGTGGTT ACGAGTTGCT CTTGGCTAAC GATATCGACA ACTCTAACCC AGCTGTTCAG    1680

GCAGAGCAAC TAAACTGGCT CCACTACATC ATGAACATTG GTTCTATCCT TGGCAATGAT    1740

CCAAGTGCCA ACTTTGACGG TGTTCGTATC GATGCGGTGG ACAATGTGGA TGCGGATCTC    1800

TTGCAGATTG CTTCTGATTA CTTCAAGGAA AAATACCGTG TCGCAGATAA TGAAGCAAAT    1860

GCCATTGCTC ATTTGTCAAT CCTTGAAGCT TGGTCATACA ACGACCACCA ATACAACAAG    1920

GATACCAAGG GTGCTCAGTT GTCTATCGAC AATCCACTAC GTGAAACGCT TTTGACGACT    1980

TTCTTGCGTA AGAGCAATTA CCGTGGCAGC TTGGAGCGCG TGATTACTAA CTCTCTTAAC    2040

AATCGTTCAA GTGAGCAGAA ACACACGCCA CGTGATGCCA ATTATATTTT CGTGCGAGCC    2100

CATGATAGTG AAGTGCAAGC TGTTTTGGCT AATATCATCA GCAAGCAGAT TAATCCAAAA    2160

ACAGATGGTT TCACCTTCAC TATGGATGAG CTCAAACAGG CCTTCGAAAT CTACAATGCG    2220

GACATCGCGA AGGCTGATAA AAAGTACACC CAGTACAATA TCCCAGCTGC CTATGCCACA    2280

ATGTTGACCA ACAAGGATAG TATCACTCGT GTTTACTACG GGACCTCTT TACCGACGAT     2340

GGCCAATACA TGGCTAAAAA ATCACCGTAC TATAATGCCA TCGATGCCCT GCTCCGTGCT    2400

CGCATCAAAT ATGTAGCAGG TGGTCAAGAC ATGAAGGTTA CTAAGCTTAA TGGCTATGAA    2460

ATCATGTCAT CTGTGCGTTA TGGTAAGGGG GCAGAAGAAG CCAACCAGCT TGGTACTGCT    2520

GAAACACGCA ACCAAGGAAT GCTGGTCCTT ACAGCCAACC GTCCAGATAT GAAGTTGGGA    2580

GCTAATGATC GTCTGGTAGT CAATATGGGA GCTGCCCACA AAAATCAGGC TTACCGTCCA    2640

TTGCTTCTCA GCAAATCGAC AGGTCTTGCG ACCTACCTCA AGGATTCTGA TGTACCAGCT    2700

GGATTGGTTC GCTATACGGA CAATCAAGGG AACTTGACCT TCACGGCAGA TGATATTGCT    2760

GGTCATTCAA CCGTTGAAGT TTCAGGTTAT TTGGCAGTTT GGGTGCCAGT GGGTGCCTCA    2820

GAAAACCAAG ATGCCCGAAC CAAGGCTTCG AGCACCAAGA AGGGTGAGCA GGTCTTTGAA    2880

TCATCAGCAG CTCTTGATTC ACAAGTCATT TACGAAGGCT TCTCAAACTT CCAAGATTTC    2940

GTTAAGACAC CAAGTCAGTA CACCAACCGT GTTATTGCTC AAAATGCCAA ACTCTTCAAA    3000

GAGTGGGGAA TCACTTCCTT TGAATTTGCG CCACAGTATG TGTCTAGCCA AGACGGCACT    3060

TTCTTGGATT CTATCATTGA AAATGGCTAC GCCTTCGAGG ACCGCTACGA TATTGCCATG    3120

AGCAAGAACA ACAAATACGG TTCACTCAAA GACCTCATGG ATGCCCTTCG TGCCCTTCAC    3180

GCAGAAGGTA TCTCAGCCAT TGCTGACTGG GTTCCAGATC AAATTTACAA TCTCCCTGGA    3240

AAAGAAGTGG TAACAGCTTC TCGTACCAAT AGCTACGGTA CACCACGTCC AAATGCTGAA    3300

ATCTACAATA GCCTCTACGC AGCTAAAACA CGTACCTTTG GAAATGACTT CCAAGGCAAG    3360

TACGGTGGTG CCTTCCTTGA TGAATTGAAG GCAAAATACC CAGCAATCTT TGAGCGCGTG    3420

CAGATTTCAA ACGGCCGTAA ATTGACTACC AATGAGAAAA TCACGCAATG GTCAGCCAAG    3480

TATTTCAATG GAAGCAATAT CCAAGGTACT GGAGCTCGCT ATGTCCTACA AGATAACGCT    3540

ACCAACCAAT ACTTCAGCGT CAAAGCAGGT CAAACCTTCC TTCCTAAACA AATGACTGAA    3600

ATTACTGAA GTGGTTTCCG TAGGGTTGGA GATGATGTCC AATACCTCTC AATTGGTGGC    3660

TACCTTGCTA AGAATACCTT TATTCAAGTC GGTGCCAACC AGTGGTATTA CTTTGATAAG    3720

AATGGCAACA TGGTCACAGG TGAGCAGGTC ATTGATGGCA AGAAATACTT CTTCCTAGAC    3780

AATGGTCTCC AGCTACGTCA TGTCCTTCGC CAAGGTAGTG ATGGTCATGT GTATTATTAC    3840
```

-continued

```
GATCCTAAAG GGGTTCAGGC CTTTAACGGA TTTTATGATT TTGCGGGTCC TCGCCAAGAC    3900

GTTCGCTACT TTGATGGCAA CGGTCAAATG TATCGTGGCC TCCACGACAT GTATGGCACA    3960

ACCTTCTATT TTGATGAAAA GACTGGTATT CAAGCCAAAG ACAAGTTCAT CCGTTTTGCG    4020

GACGGACGCA CGCGTTACTT CATCCCAGAT ACAGGAAATC TCGCAGTCAA CCGATTTGCG    4080

CAAAATCCTG AGAACAAGGC TTGGTATTAC CTCGATAGCA ACGGTTATGC CGTGACAGGA    4140

CTACAAACCA TTAACGGTAA GCAGTATTAC TTTGACAATG AAGGACGTCA GGTTAAGGGA    4200

CACTTTGTCA CTATCAATAA CCAACGTTAC TTCCTTGATG GTGATAGTGG TGAAATTGCT    4260

CCGTCACGCT TTGTGACGGA AAACAACAAG TGGTACTATG TCGATGGCAA TGGTAAACTG    4320

GTTAAAGGTG CTCAGGTCAT CAATGGTAAT CACTACTATT TCAACAATGA TTATAGCCAA    4380

GTCAAGGGTG CCTGGGCCAA CGGCCGTTAC TATGATGGTG ACTCAGGTCA GGCCGTAAGC    4440

AACCAATTCA TTCAAATTGC GGCTAACCAA TGGGCTTACC TTAACCAAGA TGGTCACAAA    4500

GTAACAGGTC TTCAAAATAT TAACAATAAA GTTTACTATT TTGGTAGCAA TGGTGCTCAA    4560

GTCAAAGGTA AATTGCTCAC TGTCCAAGGT AAGAAATGTT ACTTTGATGC CCACACAGGT    4620

GAGCAAGTGG TAAACCGCTT TGTCGAAGCT GCACGTGGCT GCTGGTATTA CTTTAACTCA    4680

GCTGGCCAAG CAGTGACTGG ACAACAGGTC ATCAATGGTA AACAACTTTA CTTCGACGGT    4740

TCAGGTCGTC AAGTTAAAGG ACGTTATGTT TATGTTGGTG GTAAACGACT CTTCTGCGAT    4800

GCCAAAACTG GTGAATTGAG ACAGCGTCGC TAATTAATAT GTACTTTAAA AAT           4853
```

(2) INFORMATION FOR SEQ ID NO:2:

(i) SEQUENCE CHARACTERISTICS:
        (A) LENGTH: 1577 amino acids
        (B) TYPE: amino acid
        (C) STRANDEDNESS:
        (D) TOPOLOGY: Not Relevant (ii) MOLECULE TYPE: protein (vi) ORIGINAL SOURCE:
        (A) ORGANISM: Streptococcus salivarius (xi) SEQUENCE DESCRIPTION: SEQ ID NO:2:

```
Met Glu Asn Lys Val Arg Phe Lys Leu His Lys Val Lys Lys Asn Trp
1               5                   10                  15

Val Thr Ile Gly Val Thr Thr Leu Ser Met Val Ala Leu Ala Gly Gly
            20                  25                  30

Ser Leu Leu Ala Gln Gly Lys Val Glu Ala Asp Glu Thr Ser Ala Pro
        35                  40                  45

Asn Gly Asp Gly Leu Gln Gln Leu Ser Glu Asp Gly Thr Ala Ser Leu
    50                  55                  60

Val Thr Thr Thr Thr Val Thr Glu Gln Ala Ser Ala Gln Ala Ser Val
65                  70                  75                  80

Ser Ala Val Ala Thr Ala Ser Val Ser His Glu Thr Ser Phe Gln Ala
                85                  90                  95

Ala Thr Ser Ala Val Ser Gln Glu Ala Thr Ala Gln Ala Gln Thr Ser
            100                 105                 110

Pro Val Ala Ser Gln Glu Val Ala Val Ser Ser Gln Thr Gln Ser Ser
        115                 120                 125

Gly Gln Glu Thr Gln Thr Thr Glu Gln Val Ser Gln Gly Gln Thr Ser
    130                 135                 140

Thr Gln Val Ala Gly Gln Thr Ser Ala Gln Ser Thr Pro Ser Val Thr
145                 150                 155                 160
```

-continued

```
Glu Gln Ala Arg Pro Arg Val Leu Thr Asn Ala Ala Pro Ala Ile Ala
            165                 170                 175

Thr Arg Ala Ala Asp Ser Thr Ile Arg Ile Asn Ala Asn Arg Asn Thr
        180                 185                 190

Asn Ile Thr Ile Thr Ala Ser Gly Thr Thr Pro Asn Val Thr Ile Ile
    195                 200                 205

Thr Gly Pro Asn Thr Pro Lys Pro Asn Val Thr Ser Pro Asn
210                 215                 220

Gly Thr Arg Pro Asn Val Thr Ile Val Thr Gln Pro Asn Gln Pro Asn
225                 230                 235                 240

Lys Pro Val Gln Pro Ser Gln Pro Ser Gln Pro Asn Lys Pro Val Gln
                245                 250                 255

Pro Asn Gln Pro Ser Leu Asp Tyr Lys Pro Val Ala Ser Asn Leu Lys
            260                 265                 270

Thr Ile Asp Gly Lys Gln Tyr Tyr Val Glu Asn Gly Val Val Lys Lys
        275                 280                 285

Asn Ala Ala Ile Glu Leu Asp Gly Arg Leu Tyr Tyr Phe Asp Glu Thr
    290                 295                 300

Gly Ala Met Val Asp Gln Ser Lys Pro Leu Tyr Arg Ala Asp Ala Ile
305                 310                 315                 320

Pro Asn Asn Ser Ile Tyr Ala Val Tyr Asn Gln Ala Tyr Asp Thr Ser
                325                 330                 335

Ser Lys Ser Phe Glu His Leu Asp Asn Phe Leu Thr Ala Asp Ser Trp
            340                 345                 350

Tyr Arg Pro Lys Gln Ile Leu Lys Asp Gly Lys Asn Trp Thr Ala Ser
        355                 360                 365

Thr Glu Lys Asp Tyr Arg Pro Leu Leu Met Thr Trp Trp Pro Asp Lys
    370                 375                 380

Val Thr Gln Val Asn Tyr Leu Asn Tyr Met Ser Gln Gln Gly Phe Gly
385                 390                 395                 400

Asn Lys Thr Tyr Thr Thr Asp Met Met Ser Tyr Asp Leu Ala Ala Ala
                405                 410                 415

Ala Glu Thr Val Gln Arg Gly Ile Glu Glu Arg Ile Gly Arg Glu Gly
            420                 425                 430

Asn Thr Thr Trp Leu Arg Gln Leu Met Ser Asp Phe Ile Lys Thr Gln
        435                 440                 445

Pro Gly Trp Asn Ser Glu Ser Glu Asp Asn Leu Leu Val Gly Lys Asp
    450                 455                 460

His Leu Gln Gly Gly Ala Leu Thr Phe Leu Asn Asn Ser Ala Thr Ser
465                 470                 475                 480

His Ala Asn Ser Asp Phe Arg Leu Met Asn Arg Thr Pro Thr Asn Gln
                485                 490                 495

Thr Gly Thr Arg Lys Tyr His Ile Asp Arg Ser Asn Gly Gly Tyr Glu
            500                 505                 510

Leu Leu Leu Ala Asn Asp Ile Asp Asn Ser Asn Pro Ala Val Gln Ala
        515                 520                 525

Glu Gln Leu Asn Trp Leu His Tyr Ile Met Asn Ile Gly Ser Ile Leu
    530                 535                 540

Gly Asn Asp Pro Ser Ala Asn Phe Asp Gly Val Arg Ile Asp Ala Val
545                 550                 555                 560

Asp Asn Val Asp Ala Asp Leu Leu Gln Ile Ala Ser Asp Tyr Phe Lys
                565                 570                 575

Glu Lys Tyr Arg Val Ala Asp Asn Glu Ala Asn Ala Ile Ala His Leu
            580                 585                 590
```

-continued

```
Ser Ile Leu Glu Ala Trp Ser Tyr Asn Asp His Gln Tyr Asn Lys Asp
        595                 600                 605

Thr Lys Gly Ala Gln Leu Ser Ile Asp Asn Pro Leu Arg Glu Thr Leu
        610                 615                 620

Leu Thr Thr Phe Leu Arg Lys Ser Asn Tyr Arg Gly Ser Leu Glu Arg
625                 630                 635                 640

Val Ile Thr Asn Ser Leu Asn Asn Arg Ser Ser Glu Gln Lys His Thr
                645                 650                 655

Pro Arg Asp Ala Asn Tyr Ile Phe Val Arg Ala His Asp Ser Glu Val
                660                 665                 670

Gln Ala Val Leu Ala Asn Ile Ile Ser Lys Gln Ile Asn Pro Lys Thr
        675                 680                 685

Asp Gly Phe Thr Phe Thr Met Asp Glu Leu Lys Gln Ala Phe Glu Ile
        690                 695                 700

Tyr Asn Ala Asp Ile Ala Lys Ala Asp Lys Lys Tyr Thr Gln Tyr Asn
705                 710                 715                 720

Ile Pro Ala Ala Tyr Ala Thr Met Leu Thr Asn Lys Asp Ser Ile Thr
                725                 730                 735

Arg Val Tyr Tyr Gly Asp Leu Phe Thr Asp Gly Gln Tyr Met Ala
                740                 745                 750

Glu Lys Ser Pro Tyr Tyr Asn Ala Ile Asp Ala Leu Leu Arg Ala Arg
        755                 760                 765

Ile Lys Tyr Val Ala Gly Gly Gln Asp Met Lys Val Thr Lys Leu Asn
        770                 775                 780

Gly Tyr Glu Ile Met Ser Ser Val Arg Tyr Gly Lys Gly Ala Glu Glu
785                 790                 795                 800

Ala Asn Gln Leu Gly Thr Ala Glu Thr Arg Asn Gln Gly Met Leu Val
                805                 810                 815

Leu Thr Ala Asn Arg Pro Asp Met Lys Leu Gly Ala Asn Asp Arg Leu
        820                 825                 830

Val Val Asn Met Gly Ala Ala His Lys Asn Gln Ala Tyr Arg Pro Leu
        835                 840                 845

Leu Leu Ser Lys Ser Thr Gly Leu Ala Thr Tyr Leu Lys Asp Ser Asp
        850                 855                 860

Val Pro Ala Gly Leu Val Arg Tyr Thr Asp Asn Gln Gly Asn Leu Thr
865                 870                 875                 880

Phe Thr Ala Asp Asp Ile Ala Gly His Ser Thr Val Glu Val Ser Gly
                885                 890                 895

Tyr Leu Ala Val Trp Val Pro Val Gly Ala Ser Glu Asn Gln Asp Ala
                900                 905                 910

Arg Thr Lys Ala Ser Ser Thr Lys Lys Gly Glu Gln Val Phe Glu Ser
        915                 920                 925

Ser Ala Ala Leu Asp Ser Gln Val Ile Tyr Glu Gly Phe Ser Asn Phe
        930                 935                 940

Gln Asp Phe Val Lys Thr Pro Ser Gln Tyr Thr Asn Arg Val Ile Ala
945                 950                 955                 960

Gln Asn Ala Lys Leu Phe Lys Glu Trp Gly Ile Thr Ser Phe Glu Phe
                965                 970                 975

Ala Pro Gln Tyr Val Ser Ser Gln Asp Gly Thr Phe Leu Asp Ser Ile
                980                 985                 990

Ile Glu Asn Gly Tyr Ala Phe Glu Asp Arg Tyr Asp Ile Ala Met Ser
        995                 1000                1005

Lys Asn Asn Lys Tyr Gly Ser Leu Lys Asp Leu Met Asp Ala Leu Arg
```

-continued

```
                   1010                 1015                 1020
Ala Leu His Ala Glu Gly Ile Ser Ala Ile Ala Asp Trp Val Pro Asp
1025                 1030                 1035                 1040
Gln Ile Tyr Asn Leu Pro Gly Lys Glu Val Val Thr Ala Ser Arg Thr
                     1045                 1050                 1055
Asn Ser Tyr Gly Thr Pro Arg Pro Asn Ala Glu Ile Tyr Asn Ser Leu
                 1060                 1065                 1070
Tyr Ala Ala Lys Thr Arg Thr Phe Gly Asn Asp Phe Gln Gly Lys Tyr
        1075                 1080                 1085
Gly Gly Ala Phe Leu Asp Glu Leu Lys Ala Lys Tyr Pro Ala Ile Phe
    1090                 1095                 1100
Glu Arg Val Gln Ile Ser Asn Gly Arg Lys Leu Thr Thr Asn Glu Lys
1105                 1110                 1115                 1120
Ile Thr Gln Trp Ser Ala Lys Tyr Phe Asn Gly Ser Asn Ile Gln Gly
                 1125                 1130                 1135
Thr Gly Ala Arg Tyr Val Leu Gln Asp Asn Ala Thr Asn Gln Tyr Phe
                     1140                 1145                 1150
Ser Val Lys Ala Gly Gln Thr Phe Leu Pro Lys Gln Met Thr Glu Ile
        1155                 1160                 1165
Thr Gly Ser Gly Phe Arg Arg Val Gly Asp Asp Val Gln Tyr Leu Ser
    1170                 1175                 1180
Ile Gly Gly Tyr Leu Ala Lys Asn Thr Phe Ile Gln Val Gly Ala Asn
1185                 1190                 1195                 1200
Gln Trp Tyr Tyr Phe Asp Lys Asn Gly Asn Met Val Thr Gly Glu Gln
                 1205                 1210                 1215
Val Ile Asp Gly Lys Lys Tyr Phe Phe Leu Asp Asn Gly Leu Gln Leu
                     1220                 1225                 1230
Arg His Val Leu Arg Gln Gly Ser Asp Gly His Val Tyr Tyr Tyr Asp
        1235                 1240                 1245
Pro Lys Gly Val Gln Ala Phe Asn Gly Phe Tyr Asp Phe Ala Gly Pro
    1250                 1255                 1260
Arg Gln Asp Val Arg Tyr Phe Asp Gly Asn Gly Gln Met Tyr Arg Gly
1265                 1270                 1275                 1280
Leu His Asp Met Tyr Gly Thr Thr Phe Tyr Phe Asp Glu Lys Thr Gly
                 1285                 1290                 1295
Ile Gln Ala Lys Asp Lys Phe Ile Arg Phe Ala Asp Gly Arg Thr Arg
                     1300                 1305                 1310
Tyr Phe Ile Pro Asp Thr Gly Asn Leu Ala Val Asn Arg Phe Ala Gln
        1315                 1320                 1325
Asn Pro Glu Asn Lys Ala Trp Tyr Tyr Leu Asp Ser Asn Gly Tyr Ala
    1330                 1335                 1340
Val Thr Gly Leu Gln Thr Ile Asn Gly Lys Gln Tyr Tyr Phe Asp Asn
1345                 1350                 1355                 1360
Glu Gly Arg Gln Val Lys Gly His Phe Val Thr Ile Asn Asn Gln Arg
                 1365                 1370                 1375
Tyr Phe Leu Asp Gly Asp Ser Gly Glu Ile Ala Pro Ser Arg Phe Val
                     1380                 1385                 1390
Thr Glu Asn Asn Lys Trp Tyr Tyr Val Asp Gly Asn Gly Lys Leu Val
        1395                 1400                 1405
Lys Gly Ala Gln Val Ile Asn Gly Asn His Tyr Tyr Phe Asn Asn Asp
    1410                 1415                 1420
Tyr Ser Gln Val Lys Gly Ala Trp Ala Asn Gly Arg Tyr Tyr Asp Gly
1425                 1430                 1435                 1440
```

```
-continued

Asp Ser Gly Gln Ala Val Ser Asn Gln Phe Ile Gln Ile Ala Ala Asn
            1445            1450            1455

Gln Trp Ala Tyr Leu Asn Gln Asp Gly His Lys Val Thr Gly Leu Gln
            1460            1465            1470

Asn Ile Asn Asn Lys Val Tyr Tyr Phe Gly Ser Asn Gly Ala Gln Val
            1475            1480            1485

Lys Gly Lys Leu Leu Thr Val Gln Gly Lys Lys Cys Tyr Phe Asp Ala
            1490            1495            1500

His Thr Gly Glu Gln Val Val Asn Arg Phe Val Glu Ala Ala Arg Gly
1505            1510            1515            1520

Cys Trp Tyr Tyr Phe Asn Ser Ala Gly Gln Ala Val Thr Gly Gln Gln
            1525            1530            1535

Val Ile Asn Gly Lys Gln Leu Tyr Phe Asp Gly Ser Gly Arg Gln Val
            1540            1545            1550

Lys Gly Arg Tyr Val Tyr Val Gly Gly Lys Arg Leu Phe Cys Asp Ala
            1555            1560            1565

Lys Thr Gly Glu Leu Arg Gln Arg Arg
1570            1575
```

LIST OF REFERENCES

1. Radojevic et al. 1994 *Aust J Agric Res* 45, 901–12.
2. Jacques N A, Giffard P M, "The Glycosyltransferases of Oral Streptococci" *Todays Life Science* 1991; 3: 40–6.
3. Walker G J, Jacques N A, "Polysaccharides of Oral Streptococci" In: Reizer J, Peterkofsky A, Eds. "*Sugar Transport and Metabolism in Gram-Positive Bacteria*". Chichester: Ellis Horwood, 1987; 39–68.
4. Gilmore K S, Russell R R B, Ferretti J J, "Anaylsis of the Streptococcus downei gtfS gene, which specifies a glucosyltransferase that synthesises soluble glucans". *Infect Immun* 1990; 58: 2452–8.
5. Giffard P M, Simpson C L, Milward C P, Jacques N A, "Molecular characterization of a cluster of at least two glucosyltransferase genes in *Streptococcus salivarius* ATCC25975". *J. Gen. Microbiol.* 1991; 137:2577–93.
6. Giffard P M, Allen D M, Milward C P, Simpson C L, Jacques N A, "Sequence of the GtfK of *Streptococcus salivarius* ATCC25975 and the evolution of the gtf genes of oral streptococci". *J Gen Microbiol* 1993; 139:1511–22.
7. Pitty L S, Giffard P M, Gilpin M L, Russell R R B and Jacques N A, 1989. "Cloning and expression of glycosyltransferase C gene (gtfC) from *Streptococcus mutans* LM7. *Infect Immun* 55: 2176–2182.
8. Silliary T S, Berman M L, and Enquist L W, 1984. "Experiments with Gene fusions". *Cold Spring Harbor Laboratory*, Cold Spring Harbor, N.Y.
9. Jacques N. A. 1983. Membrane perturbation by cerulenin modulates glucosyltransferase secretion and acetate uptake by *Streptococcus salivarius. J. Gen. Micriobial.* 129 : 3293–3302.
10. Maniatis T, Fritsch E F, and Sambrook J. (1989). "Molecular Cloning; a laboratory manual. Second edition. Cold Spring Harbor Laboratory Press, N.Y.

We claim:

1. An isolated DNA which comprises the sequence shown in SEQ ID NO: 1.
2. The plasmid pGSG501 containing λC-13 DNA.
3. The plasmid pGSG502 containing λC-13 DNA.
4. An isolated DNA which consists of the sequence shown in SEQ ID NO: 1.
5. A composition containing a DNA which comprises the sequence shown in SEQ ID NO: 1.
6. An isolated *Streptococcus salivarius* gtfM gene which encodes a primer independent glucosyltransferase which produces soluble glucans from sucrose.
7. A plant transformed with a gene according to claim 6.
8. A plant transformed with a DNA according to claims 1 or 4.
9. A plant transformed with a composition according to claim 5.
10. A method of increasing the level of stored carbohydrate in a pasture plant with low levels of carbohydrate, the method comprising inserting into the plant DNA comprising a sequence which encodes an amino acid sequence according to SEQ ID NO:2 so that the plant expresses said amino acid sequence, wherein the amino acid sequence increases the level of stored carbohydrate in the plant.
11. A method of increasing the level of stored carbohydrate in a pasture plant with low levels of carbohydrate, the method comprising inserting DNA according to claim 1 or claim 4 into the plant so that the plant expresses an amino acid sequence encoded by the DNA, wherein the amino acid sequence increases the level of stored carbohydrate in the plant.
12. A method of increasing the level of stored carbohydrate in a pasture plant with low levels of carbohydrate, the method comprising inserting a DNA-containing composition according to claim 5 into the plant so that the plant expresses an amino acid sequence encoded by the DNA containing composition, wherein the amino acid sequence increases the level of stored carbohydrate in the plant.
13. A method of increasing the level of stored carbohydrate in a pasture plant with low levels of carbohydrate, the method comprising inserting a gene according to claim 6 into the plant so that the plant expresses an amino acid sequence encoded by the gene, wherein the amino acid sequence increases the level of stored carbohydrate in the plant.
14. A method of preventing degradation of stored carbohydrate during senescence in a pasture plant, the method comprising inserting into the plant a DNA comprising a sequence which encodes an amino acid sequence according to SEQ ID NO:2 so that the plant expresses said amino acid sequence, wherein the amino acid sequence prevents degradation of stored carbohydrate in the pasture plant during senescence.

15. A method of preventing degradation of stored carbohydrate during senescence in a pasture plant, the method comprising inserting a DNA according to claim 1 or 4 into the plant so that the plant expresses an amino acid sequence encoded by the DNA, wherein the amino acid sequence prevents degradation of stored carbohydrate in the pasture plant during senescence.

16. A method of preventing degradation of stored carbohydrate during senescence in a pasture plant, the method comprising inserting a DNA containing-composition according to claim 5 into the plant so that the plant expresses an amino acid sequence encoded by the DNA containing composition, wherein the amino acid sequence prevents degradation of stored carbohydrate in the pasture plant during senescence.

17. A method of preventing degradation of stored carbohydrate during senescence in a pasture plant, the method comprising inserting a gene according to claim 6 into the plant so that the plant expresses an amino acid sequence encoded by the gene, wherein the amino acid sequence prevents degradation of stored carbohydrate in the pasture plant during senescence.

* * * * *